(12) United States Patent
Blomquist et al.

(10) Patent No.: US 7,734,323 B2
(45) Date of Patent: Jun. 8, 2010

(54) CORRECTION FACTOR TESTING USING FREQUENT BLOOD GLUCOSE INPUT

(75) Inventors: Michael Blomquist, Blaine, MN (US); Rhall E. Pope, Minneapolis, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 92 days.

(21) Appl. No.: 11/626,653

(22) Filed: Jan. 24, 2007

(65) Prior Publication Data

US 2008/0177165 A1 Jul. 24, 2008

(51) Int. Cl.
*A61B 5/00* (2006.01)
(52) U.S. Cl. .................................. 600/347; 600/365
(58) Field of Classification Search .............. 600/365; 604/65
See application file for complete search history.

(56) References Cited

U.S. PATENT DOCUMENTS

| | | |
|---|---|---|
| 5,181,910 A | 1/1993 | Scanlon |
| 5,338,157 A | 8/1994 | Blomquist |
| 5,368,562 A | 11/1994 | Blomquist et al. |
| 5,389,078 A | 2/1995 | Zalesky et al. |
| 5,485,408 A | 1/1996 | Blomquist |
| 5,569,186 A * | 10/1996 | Lord et al. ............... 604/67 |
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,695,473 A | 12/1997 | Olsen |
| 5,810,771 A | 9/1998 | Blomquist |
| 5,822,715 A | 10/1998 | Worthington et al. |
| 5,876,370 A | 3/1999 | Blomquist |
| 5,879,143 A | 3/1999 | Cote et al. |
| 5,935,099 A | 8/1999 | Peterson et al. |
| 5,935,106 A | 8/1999 | Olsen |
| 6,024,539 A | 2/2000 | Blomquist |

(Continued)

FOREIGN PATENT DOCUMENTS

EP  1571582 A2  9/2005

(Continued)

OTHER PUBLICATIONS

Walsh, John, et al., "Select & Test Your Correction Factor", *Pumping Insulin*, Fourth Edition, Chapter 13, (2006), 29 Pages.

(Continued)

*Primary Examiner*—Robert L Nasser
(74) *Attorney, Agent, or Firm*—Schwegman, Lundberg & Woessner, P.A.

(57) ABSTRACT

An apparatus comprising a user interface configured to generate an electrical signal to begin determination of an effective correction factor when prompted by a user, an input configured to receive sampled blood glucose data of a patient that is obtained during a specified time duration, including a time duration after delivery of an initial insulin correction bolus, and a controller in electrical communication with the input and the user interface. The controller includes a correction factor module configured for determining an effective correction factor according to an amount of insulin in the initial insulin correction bolus and a decrease in the blood glucose level determined using the sampled blood glucose data. Other devices and methods are disclosed.

27 Claims, 7 Drawing Sheets

U.S. PATENT DOCUMENTS

| | | |
|---|---|---|
| 6,077,055 A | 6/2000 | Vilks |
| 6,241,704 B1 | 6/2001 | Peterson et al. |
| 6,248,057 B1 | 6/2001 | Mavity et al. |
| 6,422,057 B1 | 7/2002 | Anderson |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,641,533 B2 | 11/2003 | Causey, III et al. |
| 6,744,350 B2 | 6/2004 | Blomquist |
| 6,809,653 B1 | 10/2004 | Mann et al. |
| 6,852,104 B2 | 2/2005 | Blomquist |
| 6,872,200 B2 | 3/2005 | Mann et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,098,803 B2 | 8/2006 | Mann et al. |
| 7,109,878 B2 | 9/2006 | Mann et al. |
| 7,267,665 B2 * | 9/2007 | Steil et al. .................. 604/131 |
| 7,278,983 B2 * | 10/2007 | Ireland et al. ................ 604/66 |
| 7,307,245 B2 * | 12/2007 | Faries et al. ................. 219/413 |
| 7,324,012 B2 | 1/2008 | Mann et al. |
| 2001/0031944 A1 | 10/2001 | Peterson et al. |
| 2001/0037217 A1 * | 11/2001 | Abensour et al. .............. 705/2 |
| 2002/0183693 A1 | 12/2002 | Peterson et al. |
| 2003/0114836 A1 * | 6/2003 | Estes et al. ............... 604/890.1 |
| 2003/0212364 A1 | 11/2003 | Mann et al. |
| 2004/0073095 A1 | 4/2004 | Causey, III et al. |
| 2005/0030164 A1 | 2/2005 | Blomquist |
| 2005/0065760 A1 | 3/2005 | Murtfeldt et al. |
| 2005/0171513 A1 | 8/2005 | Mann et al. |
| 2006/0001550 A1 | 1/2006 | Mann et al. |
| 2006/0132292 A1 | 6/2006 | Blomquist |
| 2006/0202859 A1 | 9/2006 | Mastrototaro et al. |
| 2006/0253097 A1 * | 11/2006 | Braig et al. .................. 604/504 |
| 2007/0156033 A1 | 7/2007 | Causey, III et al. |
| 2008/0030369 A1 | 2/2008 | Mann et al. |
| 2008/0033357 A1 | 2/2008 | Mann et al. |
| 2008/0097289 A1 * | 4/2008 | Steil et al. ..................... 604/67 |
| 2008/0106431 A1 * | 5/2008 | Blomquist ............. 340/825.19 |
| 2008/0269585 A1 * | 10/2008 | Ginsberg .................... 600/365 |

FOREIGN PATENT DOCUMENTS

| | | |
|---|---|---|
| WO | WO-0045696 A1 | 8/2000 |
| WO | WO-0152727 A1 | 7/2001 |
| WO | WO-2008091320 A2 | 7/2008 |
| WO | WO-2008091320 A3 | 7/2008 |

OTHER PUBLICATIONS

"International Application Serial No. PCT/US2007/024424, Search Report mailed Mar. 6, 2009".

"International Application Serial No. PCT/US2007/024424, Written Opinion mailed Mar. 6, 2009".

* cited by examiner

|  |  | 0 – +1 mg/dl/min | +1 - +2 mg/dl/min | +2 - +4 mg/dl/min | 0 – -1 mg/dl/min | -1 - -2 mg/dl/min | -2 - -4 mg/dl/min |
|---|---|---|---|---|---|---|---|
| Above target | >300 | 1 | 1.2 | 1.4 | 1 | 1 | 1 |
|  | +300 | 1 | 1.2 | 1.4 | 1 | 1 | .75 |
|  | +250 | 1 | 1.2 | 1.4 | 1 | .75 | .5 |
|  | +200 | 1 | 1.2 | 1.4 | 1 | .5 | .25 |
|  | +150 | 1 | 1.2 | 1.4 | .75 | .25 | 0 |
|  | +100 | 1 | 1.2 | 1.4 | .5 | 0 | -.25 |
|  | +50 | 1 | 1.2 | 1.4 | .25 | -.25 | -.5 |
| Target | 0 |  |  |  |  |  |  |
| Below target | 10 | 1 | .8 | .6 | 1 | 1 | 1.5 |
|  | 20 | 1 | .8 | .6 | 1 | 1.25 | 1.75 |
|  | 30 | 1 | .8 | .6 | 1 | 1.5 | 2 |
|  | 40 | 1 | .8 | .6 | 1.25 | 1.75 | 2.25 |
|  | 50 | 1 | .8 | .6 | 1.5 | 2 | 2.5 |
|  | 60 | 1 | .8 | .6 | 1.75 | 2.25 | 2.75 |

CORRECTION FACTOR TESTING USING FREQUENT BLOOD GLUCOSE INPUT

TECHNICAL FIELD

The field generally relates to patient insulin management devices and, in particular, but not by way of limitation, to systems and methods for adjusting insulin therapy.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's blood glucose levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

Blood glucose (BG) management devices help a diabetic person manage their blood glucose. For example, an insulin pump is a BG management device that provides insulin throughout the day. A glucose monitor (GM) or meter is a BG management device to measure blood glucose levels. Some monitors require a finger-stick to acquire a sample of blood that is applied to a test strip to get a blood glucose reading. Some monitors are able to provide continuous monitoring of blood glucose. Other BG management devices include computers running software to help a diabetic person manage insulin therapy. However, most BG management devices are limited in the control over blood glucose that they offer.

SUMMARY

This document discusses, among other things, apparatuses and methods for managing insulin therapy. An apparatus example includes a user interface configured to generate an electrical signal to begin determination of an effective correction factor when prompted by a user, an input configured to receive sampled blood glucose data of a patient that is obtained during a specified time duration (including a time duration after delivery of an initial insulin correction bolus), and a controller in electrical communication with the input and the user interface. The controller includes a correction factor module configured for determining an effective correction factor according to an amount of insulin in the initial insulin correction bolus and a decrease in the blood glucose level determined using the sampled blood glucose data.

A method example includes receiving a user prompt in a blood glucose (BG) management device to start a determination of an effective correction factor, receiving sampled blood glucose data of a patient obtained during a specified time duration, including a time duration after delivery of an initial insulin correction bolus, and determining the effective correction factor using the BG management device according to a determined decrease in the blood glucose level of the patient and an amount of insulin in the initial insulin correction bolus.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

FIG. 3 is an example of a look-up table that includes rate of change of blood glucose.

DETAILED DESCRIPTION

Figure 1:
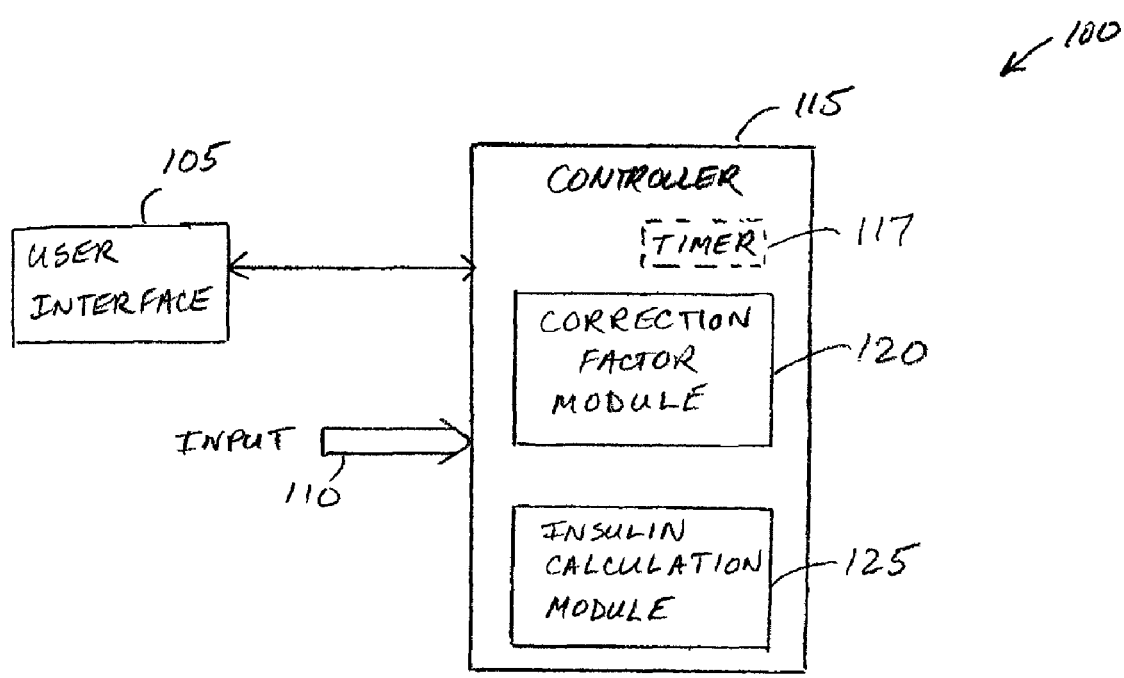
FIG. 1 is a block diagram of portions of a blood glucose (BG) management device.

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly use and program the pump.

A correction factor refers to the amount in drop in blood sugar, or blood glucose, for one unit of insulin. It is measured in milligrams per deciliter (mg/dl) per unit in the U.S. and in millimoles (mmol) per unit in other countries. A pump uses the correction factor to automatically determine a bolus amount required for a high reading or a reduction in a meal bolus for a below-target reading. A pump may also use the correction factor to calculate the amount of carbohydrates a patient should eat to bring low blood sugar up to a target blood sugar level. An appropriate correction factor brings a high blood glucose reading down using an automatically determined correction bolus without a risk of going low.

The appropriate correction factor varies from person to person. It is important for a pump to use an effective correction factor. If a correction factor for a pump is set too high, the blood glucose may not actually be dropping as much as estimated and could lead to high blood glucose levels. If the correction factor is set too low, a correction bolus may provide too much insulin and result in a low blood glucose level.

Typically, the correction factor for a pump is initially entered by a clinician based on a total daily dose (TDD) of insulin for the diabetic person. The clinician may use a rule such as the "1800 rule" in setting the correction factor. For example, if a person's TDD is 40 units of insulin, the correction factor would be 1800/40 or 45 mg/dl per unit. (The 1800 rule corresponds to a "100 rule" if mmol are used.) The clinician may also take into account factors such as a person's age, weight, and activity level when setting the correction factor. Other calculations include the 1700 rule (94 rule if mmol) and the 1500 rule (83 rule if mmol). For example, under the 1700 rule the correction factor would be 1700/40 or 42.5 mg/dl. A clinician may prefer one rule over another based on experience including rules that are not based on TDD.

Once an approximate correction factor has been established using TDD or some other method, the patient's actual or most effective correction factor should be determined. However, determining such a correction factor is complicated by the fact that an appropriate correction factor varies from person to person, may be different for a person at various times of the day, and may change for a person over time. A diligent insulin pump user may adjust their correction factor many times as they try to find their appropriate correction factor and determine how it may vary with time and how it may vary under other circumstances. Blood glucose (BG) management devices are more valuable to a diabetic person if the device conveniently assists them in determining their appropriate correction factor.

Apparatus Embodiments

FIG. 1 is a block diagram of portions of a BG management device 100. Examples of a BG management device 100 include, among other devices, an insulin pump, a blood glucose monitor (GM) or meter, and a computing device running software to assist a diabetic patient in managing insulin therapy. The BG management device 100 includes a user interface 105, an input 110, and a controller 115 in electrical communication with the input 110 and the user interface 105. The user interface 105 generates an electrical signal to begin determination of an effective correction factor when prompted by a user. The user interface may include a pushbutton, keypad, or a computer mouse. The user interface may include a display to provide instructions to the user. The display may include a touch-screen. The user of the device may be a clinician or a diabetic patient. The user prompts the BG management device 100 using the user interface 105 to begin a correction factor test. The correction factor test assists the patient in determining an effective correction factor.

As part of the correction factor test, the patient receives an initial insulin correction bolus. If the BG management device 100 includes an insulin pump, the insulin correction bolus may be delivered using the BG management device 100. If the BG management device 100 does not include an insulin pump, the insulin correction bolus may be delivered using a separate device that includes an insulin pump or may be delivered by injection.

The input 110 is configured to receive sampled blood glucose data of the patient as part of the correction factor test. The blood glucose data is obtained during a specified time duration. The specified time duration includes a time after delivery of the initial insulin correction bolus, but may include a time prior to the delivery of the initial insulin correction bolus as well. The configuration of the input 110 may depend on the type of BG management device 100. If the BG management device 100 is an insulin pump, the input 110 may be coupled to a GM included in the pump or the input 110 may include a communication port to receive the blood glucose data from a second device. In some embodiments, the input 110 is coupled to the user interface 105, and the user may manually input the data into the pump through a keypad or keyboard included in the user interface.

If the BG management device 100 includes a GM, the input 110 may be coupled to blood glucose sensor circuit. The blood glucose sensor circuit includes a blood glucose sensor to produce a blood glucose signal representative of a blood glucose level of the patient. The blood glucose sensor circuit may include a sensor interface circuit to sample the blood glucose signal and may provide additional signal processing such as filtering for example. The blood glucose sensor circuit provides the sampled blood glucose data to the input 110. If the device includes neither a pump nor a GM, such as if the BG management device 100 is a computing device, the input 110 may include a communication port to receive the blood glucose data from a second device.

The controller 115 can be implemented using hardware circuits, firmware, software or any combination of hardware, firmware and software. Examples, include a microcontroller, a logical state machine, and a processor such as a microprocessor, application specific integrated circuit (ASIC), or other type of processor. The controller 115 includes a correction factor module 120. Modules can be software, hardware, firmware or any combination of software, hardware, and firmware. Multiple functions can be performed in one or more modules. The correction factor module 120 determines the effective correction factor according to an amount of insulin in the initial insulin correction bolus and a decrease in the blood glucose level determined using the sampled blood glucose data.

Figure 2A:
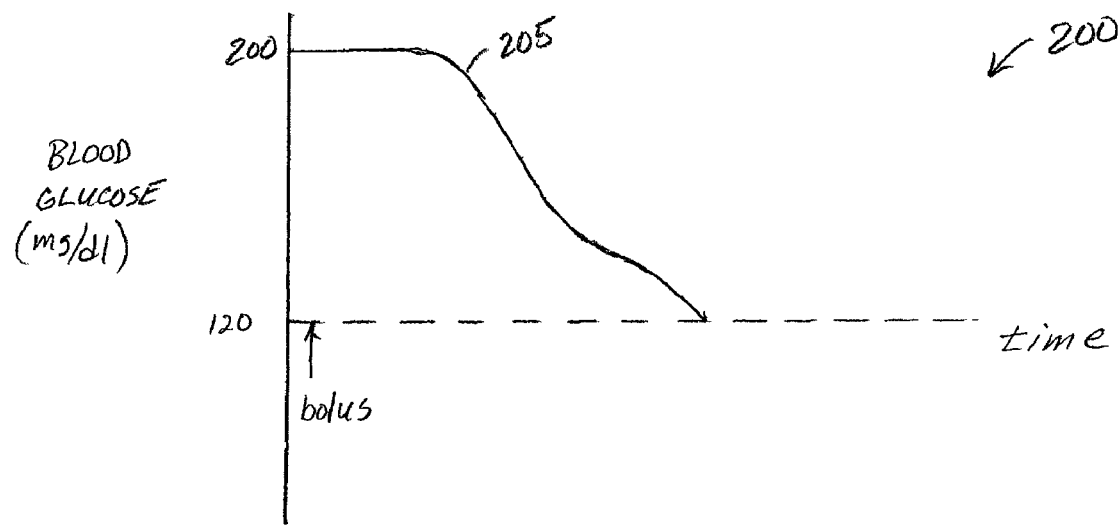
FIGS. 2A-B are example illustrations of graphs of blood glucose during a correction factor test.
Figure 2B:
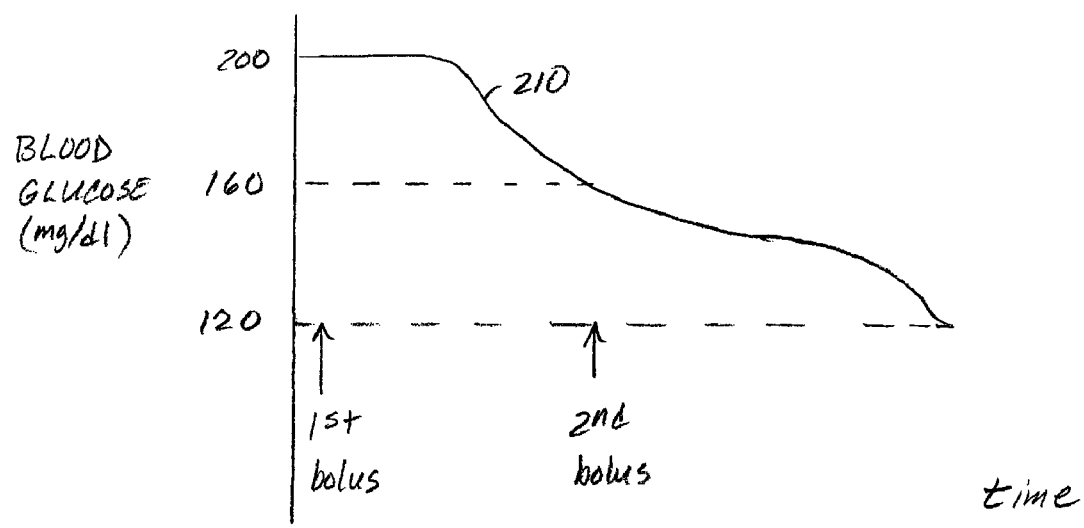

FIGS. 2A-B are example illustrations of graphs 200 of blood glucose during a correction factor test. Assume, as shown in the waveform 205 of FIG. 2A, that at the start of the test the patient's blood glucose level is 200 mg/dl. Also assume that the target blood glucose level is about 120 mg/dl. The target could also be a range such as 150 mg/dl to 100 mg/dl. If a current correction factor before the test was 80 mg/dl per unit, it would be expected that one unit of insulin would reduce the blood glucose of the patient to 120 mg/dl. If at the end of the specified time duration for the test, the blood glucose of the patient was above 120 mg/dl, the correction factor is too high. For example, if after the specified time duration for the test the blood glucose level was 140 mg/dl, the correction factor module 120 would determine the effective correction factor to be 60 mg/dl per unit.

In some embodiments, the controller 115 includes an insulin calculation module 125. The insulin calculation module 125 calculates the amount of insulin in the initial insulin correction bolus to decrease a blood glucose level of the patient within a first specified percentage of a target blood glucose baseline. The insulin calculation module 125 calculates the amount of insulin using a pre-bolus correction factor. The pre-bolus correction is the correction factor that is present in the BG management device 100 before the correction factor test.

For example, assume as in FIG. 2A, that the patient's initial blood glucose level is 200 mg/dl, the pre-bolus correction factor is 80 mg/dl per unit and a goal is to get the patient's blood glucose to 120 mg/dl. The insulin calculation module 125 determines that the amount of insulin in the initial insulin correction bolus should be one unit of insulin.

In some embodiments, the pre-bolus correction is calculated using a formula such as the 1800 rule and the correction factor is manually entered by a user through the user interface. In some embodiments, the BG management device calculates the pre-bolus correction factor. For example, the insulin calculation module 125 may be configured for receiving daily injection information (e.g., MDI information) entered by a user through the user interface 105. The daily injection information provides a measure of TDD. The insulin calculation module 125 estimates the pre-bolus correction factor using the daily injection information. For example, a clinician may prefer to program the insulin calculation module 125 to use a calculation such as the 1800 rule. The insulin calculation module 125 then estimates the pre-bolus correction factor using the TDD and the 1800 rule. In other examples, the insulin calculation module 125 may use a rule desired by a clinician that is different from the 1800 rule, 1700 rule, or 1500 rule.

The blood glucose level of the patient should be a reasonable amount above the target blood glucose level before a correction factor test to avoid a risk of going too low. In some embodiments, a conservative approach is used to make sure the blood glucose level does not go too low. For example, the controller 115 may cancel the correction factor test if a blood glucose level of the patient is outside of a specified range of blood glucose levels when the user wants to run the test. As another example, the user may elect to use a higher value for the pre-bolus correction factor to provide less risk of low blood glucose. Another conservative approach is for the controller 115 to run the test in two parts.

In the first part, the insulin calculation module 125 calculates a first insulin correction bolus to bring the blood glucose level to within a conservative percentage of the blood glucose target, such as 50% of the target for example.

This is shown by the waveform 210 in FIG. 2B. The insulin calculation module 125 uses the pre-bolus correction factor in determining the amount of insulin in the first insulin correction bolus. For example, assume the initial blood glucose level is 200 mg/dl, the pre-bolus correction factor is 80 mg/dl per unit, and the target blood glucose level is 120 mg/dl. The insulin calculation module 125 calculates a bolus of one unit. If the first specified percentage is 50% of the calculated bolus, the insulin calculation module 125 calculates the first insulin correction bolus to be 0.5 units. At the conclusion of the first part of the test, the correction factor module 120 then calculates the effective correction factor. For example, if after the first bolus, the patient's BG dropped 30 mg/dl from 200 mg/dl to 170 mg/dl, the correction factor module 125 would calculate the effective correction factor as 30 mg/dl divided by 0.5 units, or 60 mg/unit.

In the second part of the test, the insulin calculation module 125 uses the effective correction factor to calculate the amount of insulin to use in a second insulin correction bolus. The second bolus is to decrease the blood glucose level of the patient to the target blood glucose baseline. The correction factor module 120 may then recalculate the effective correction factor using the decrease in blood glucose after the second correction bolus. The two-part approach includes less risk in overshooting the target blood glucose level and may be useful if the user does not have a lot of confidence in the pre-bolus correction factor. The two-part approach also allows the correction factor module to determine if there is a difference in the effective correction factor when the absolute blood glucose value of the patient is in a higher range and when the blood glucose value of the patient is in a lower range.

In some embodiments, the insulin calculation module 125 determines an amount of carbohydrates for the patient to consume if the blood glucose level goes below the target level. For example, assume that after a correction factor test, the blood glucose level of a patient is 40 mg/dl below the target level and correction factor module 120 determines during the test that the effective correction factor was 1 unit per 80 mg/dl. The insulin calculation module 125 determines that −0.5 units of insulin (−40/80) are required to bring the blood glucose level back to the target blood glucose level. Further assume that the carbohydrate ratio of the patient is 20 grams of carbohydrates per unit of insulin (20 g/u). A carbohydrate ratio refers to the amount of carbohydrates reduced, or covered, by one unit of insulin. The insulin calculation module 125 multiplies the amount of insulin by the carbohydrate ratio to determine that the patient should eat 10 grams of carbohydrates [(0.5)(20)]. The insulin calculation module 125 may take into account additional factors such as the health status of the patient and the activity level of the patient in recommending the carbohydrate amount.

The graphs 200 in FIG. 2 show a blood glucose level of a patient at a substantial plateau before the initial insulin correction bolus is delivered. In some cases the blood glucose level of the patient may be changing when a user wants to start a correction factor test. In some embodiments, the insulin calculation module 125 determines the amount of insulin in an insulin correction bolus using a rate of change of the blood glucose level. In some embodiments, the insulin calculation module 125 uses a table look-up method.

An example of a look-up table that includes rate of change of blood glucose is shown in FIG. 3. The rows of the table correspond to pre-defined blood glucose values and an identified target blood glucose value. In the example table shown, the blood glucose values correspond to a difference between a blood glucose concentration of a patient (in mg/dl) and the target blood glucose concentration. The columns of the table correspond to pre-defined ranges of rate of change of blood glucose. In the example table, the rate of change is measured in milligrams per deciliter per minute (mg/dl/min). Each block of the table includes a multiplication factor corresponding to a blood glucose concentration and a blood glucose rate of change. In some embodiments, the blocks of the table include logic that determines a therapy action based the blood glucose concentration and the blood glucose rate of change.

If the blood glucose concentration is above the target blood glucose value and the calculated correction bolus is a positive number, the insulin calculation module 125 first calculates an amount of insulin in the insulin correction bolus without the rate of change. The insulin calculation module 125 then adjusts the insulin amount using the multiplication factor. For example, if the current correction factor is 1 u per 80 mg/dl, and the blood glucose level of the patient is 50 mg/dl above the target, the insulin correction bolus is determined to be (50/80) units or about 0.63 units. If the rate of change of the blood glucose of the patient is in the range of +1 to +2 mg/dl/min, the insulin calculation module 125 multiplies the amount by 1.2 to arrive at an adjusted amount of about 0.75 units. In some embodiments, the insulin dose is displayed as a recommendation to the user and the user accepts the recommendation, modifies the recommendation, or commands a different delivery action.

If the blood glucose concentration is below the target blood glucose value, a correction factor test will not be run. In some embodiments, the insulin calculation module 125 calculates a negative amount of insulin to required to bring the blood glucose level back to the target blood glucose value. The insulin calculation module 125 determines an amount of carbohydrates for the patient to consume using the negative insulin amount and the carbohydrate ratio as described above.

In some cases, a correction factor test will not be run if the rate of change of the blood glucose is a large and negative value, even though the blood glucose concentration is above the target blood glucose value. This situation corresponds to the shaded blocks with negative multiplication factors. Because of the negative multiplication factor, the insulin calculation module 125 will calculate a negative amount of insulin. The insulin calculation module 125 determines an amount of carbohydrates for the patient to consume using the negative insulin amount and the carbohydrate ratio as described above. For example, if the current correction factor is 1 u per 80 mg/dl, and the blood glucose level of the patient is 50 mg/dl above the target as before, the insulin correction bolus is determined to be (50/80) units or about 0.63 units. This time assume the rate of change of the blood glucose of the patient is in the range of −2 to −4 mg/dl/min. The insulin calculation module 125 multiplies the amount by −0.5 to arrive at an adjusted amount of about −0.31 units. The insulin calculation module 125 multiplies the amount of insulin by the carbohydrate ratio (20 g/u) and determines that the patient should eat 6.2 grams of carbohydrates. In some embodiments, a carbohydrate amount is displayed as a recommendation to the user.

Another example of a look-up table that includes rate of change of blood glucose is shown in Table 1 below.

TABLE 1

| BG Rate of change | Correction bolus adjustment |
|---|---|
| >+3.0 mg/dl/min | +8% |
| Between +2.1 and +3.0 mg/dl/min | +6% |
| Between +1.1 and +2.0 mg/dl/min | +4% |
| Between +.1 and +1.0 mg/dl/min | +2% |
| <+/−.1 mg/dl/min | No adjustment |
| Between −0.1 and −1.0 mg/dl/min | −2% |
| Between −1.1 and −2.0 mg/dl/min | −4% |
| Between −2.1 and 3.0 mg/dl/min | −6% |
| >−3.0 mg/dl/min | −8% |

This approach would be applicable when the patient's blood glucose level is above the target level. The left column of the table includes pre-defined ranges of rate of change of blood glucose measured in mg/dl/min. The right column includes a percentage change used to adjust the insulin correction bolus based on the rate of change. The insulin calculation module 125 calculates the standard insulin correction bolus and adjusts the bolus amount by the percentage change based on the information in the table.

The correction factor test may be a long test whether a one-part or two-part test is used. The patient may have to refrain from eating for six to eight hours for the insulin in a correction bolus to work completely. In some embodiments, the user interface 105 includes a display and the BG management device 100 displays instructions for the user during the correction factor test, such as not to eat during the test and/or to maintain a normal activity level during the test for example.

Returning to FIG. 1, the user interface 105 may include a display operatively coupled to the controller 115. Using the display, the controller 115 provides user instructions to run a correction factor test and determine an effective correction factor. It may be desirable to use different correction factors at different times during the day. For example, one correction factor may be more appropriate during a time of day when the patient is less sensitive to insulin and another correction factor may be more appropriate during a time of day when the patient is more sensitive to insulin. The BG management device 100 may include a timer circuit 117 operatively coupled to the controller 115. The controller 115 displays user instructions to determine the effective correction factor at one or more specified times during a day. In some embodiments, controller 115 displays user instructions to run the correction factor test on multiple days. The controller 115 may prompt the use to run the test during substantially the same time on the multiple days. This may result in more accurate correction factors being used at different times during the day.

Figure 4:
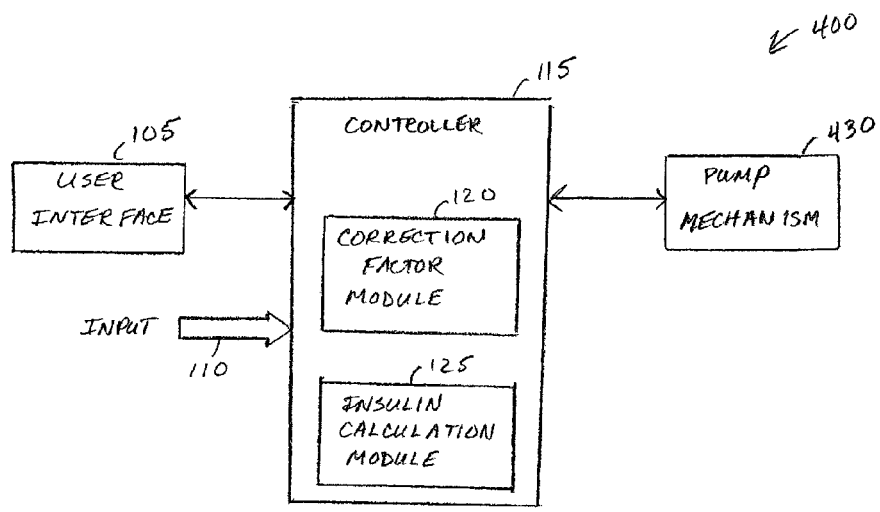
FIG. 4 is a block diagram of portions of an example of a BG management device that includes a pump mechanism.

According to some embodiments, the BG management device includes an insulin pump. FIG. 4 is a block diagram of portions of an example of a BG management device 400 that includes a pump mechanism 430 to deliver an insulin correction bolus to the patient. The pump mechanism 430 is operatively coupled to the controller 115. The controller 115 may track the amount of insulin delivered via the pump mechanism 430. The insulin may be delivered through boluses such as a correction bolus or a carbohydrate bolus. A carbohydrate bolus is an amount of insulin delivered to match carbohydrates in an upcoming meal. The insulin may also be delivered according to a basal rate pattern or profile.

In some embodiments, the insulin calculation module 125 is able to keep track of the amount of active insulin in the patient. This is sometimes referred to as insulin on board (IOB). To track the amount of active insulin, the controller 115 uses the amount of insulin delivered, the time that elapsed since delivery of insulin and a duration of how long the insulin is active in the blood. The duration may be determined using kinetic action, which is the time it takes for insulin to disappear from the blood, or the duration of insulin action (DIA), which is how long the insulin lowers blood glucose.

In some embodiments, the controller 115 cancels a correction factor test (and the delivery of an associated insulin correction bolus) if the insulin calculation module 125 determines that the active insulin amount is above a specified threshold amount. This is a conservative approach and minimizes the risk of IOB confounding the results of the correction factor test. In some embodiments, the controller 115 suspends the start of the correction factor test until the amount of active insulin becomes substantially zero.

In some embodiments, the insulin calculation module 125 uses the amount of active insulin in the patient to determine the initial insulin correction bolus amount or the second insulin correction bolus if a two-part test is used. In some examples, the insulin calculation module 125 uses the amount of active insulin and the rate of change of the blood glucose level in determining an insulin correction bolus. As an example, the insulin calculation module 125 can factor IOB into the initial correction bolus calculation and then apply a multiplication factor, such as in FIG. 3 or Table 1, to account for the rate of change.

Figure 5:
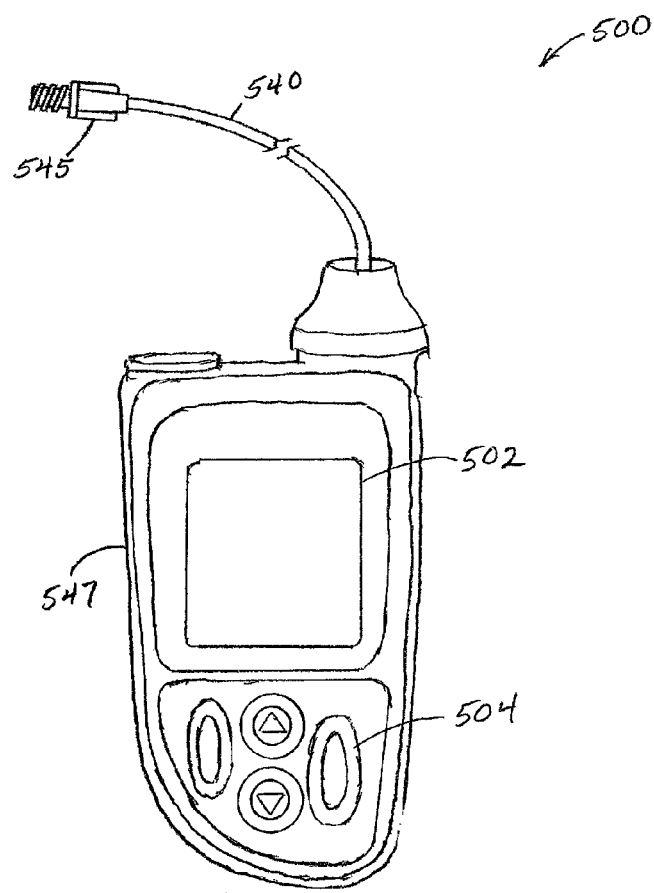
FIG. 5 is an illustration of a BG management device that includes an insulin pump.

FIG. 5 is an illustration of a BG management device 500 that includes an insulin pump. The BG management device 500 includes a cassette or cartridge of insulin and tubing 540 connectable to a patient such as by a Luer lock 545. The BG management device 500 includes a user interface that may include a display 502 in electrical communication with a controller 115. The user interface may also include one or more keys 504.

Returning to FIG. 4, the blood glucose data may be produced by a second device separate from the BG management device 400. The controller 115 displays user instructions for the determination of the effective correction factor. The user interface 105 and the input 110 are configured to receive the sampled blood glucose data entered manually by the user through the user interface 105. The controller 115 may periodically prompt the user to enter a blood glucose value at different times during the test, or to enter the blood glucose data all at once after the test.

Figure 6:
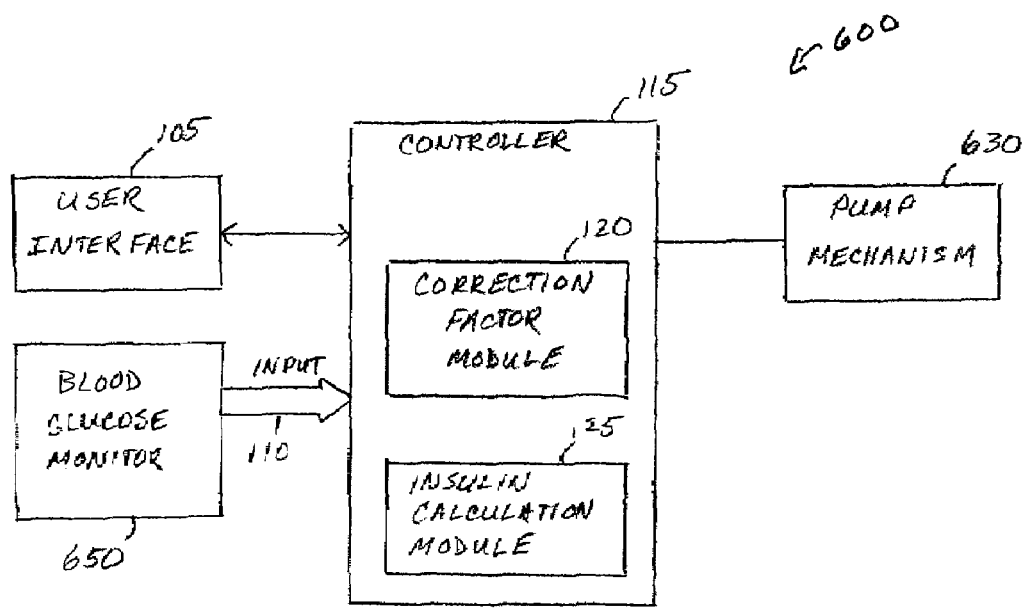
FIG. 6 is another block diagram of portions of a BG management device that includes a pump mechanism.

FIG. 6 is another block diagram of portions of a BG management device 600 that includes a pump mechanism 630. A blood glucose monitor, or GM 650, is communicatively coupled to the input 110. The input 110 is configured to receive the sampled blood glucose data from the GM 650. In some examples, the GM 650 is included in the BG management device 600 and is coupled to the input. In some examples, the GM 650 is included in a second device. The input 110 may include a communication port, such as communication port 547 located on the rear face of the device in FIG. 5, and the GM 650 is communicatively coupled to the input 110 by the communication port 547. In some embodiments, the communication port 547 is a wired port such as a serial interface or bus interface for communicating with the second device. In some embodiments, the communication port 547 is a wireless port such as an infrared (IR) communication port or a radio frequency (RF) communication port. The input wirelessly receives the sampled blood glucose data from the second device.

Returning to FIG. 6, in some embodiments, the GM 650 is a continuous GM 650 and automatically collects the sampled blood glucose data. For example, the GM 650 may include a blood glucose sensor. The blood glucose sensor produces a blood glucose signal representative of a blood glucose level of the patient. The GM 650 samples the blood glucose signal to obtain the sampled blood glucose data.

In some embodiments, the user may need to prompt the GM 650 to begin a blood glucose measurement. For example, the GM 650 may require diabetes test strips to take a blood glucose measurement. The controller 115 prompts the user, via a display, to begin a blood glucose measurement using the GM 650. The user then provides a new test strip to the GM 650 when prompted during the correction factor test. In another example, the GM 650 may include a drum of diabetes test strips and the user advances the drum to a fresh or unused test strip when prompted by the controller 115. The controller 115 may display the effective correction factor after the correction factor test. The controller 115 may also communicate the effective correction factor to the second device via the communication port.

Figure 7:
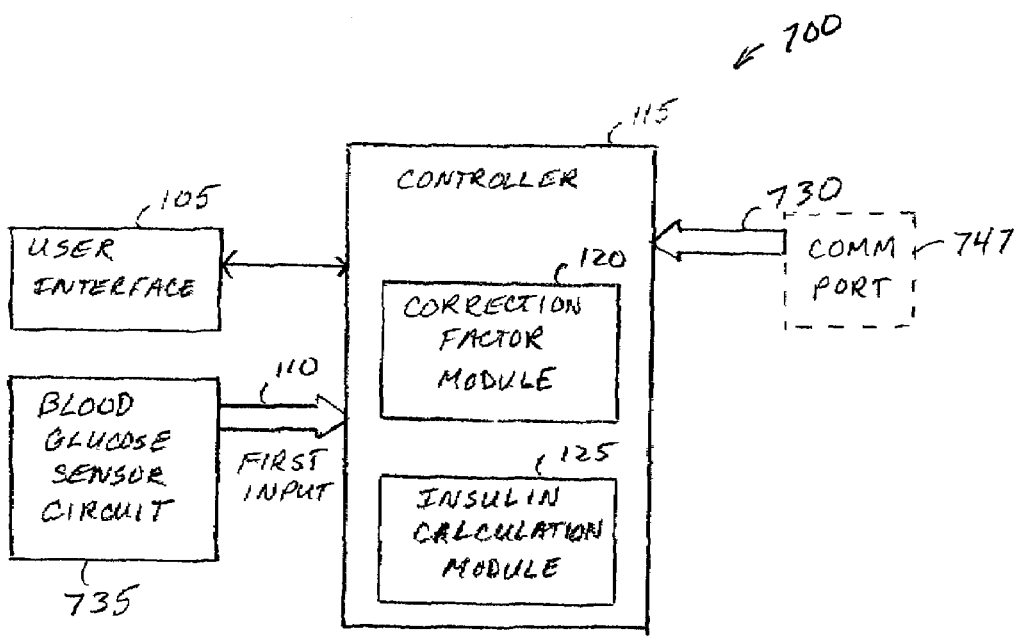
FIG. 7 is a block diagram of a BG management device that includes a blood glucose sensor circuit.

According to some embodiments, the BG management device is a GM. FIG. 7 is a block diagram of a BG management device 700 that includes a blood glucose sensor circuit 735 operatively coupled to the input 110. The blood glucose sensor circuit 735 produces a blood glucose signal representative of a blood glucose level of the patient and provides the sampled blood glucose data to input 110. In some embodiments, the blood glucose sensor circuit 735 includes an implantable blood glucose sensor. In some embodiments, the blood glucose sensor includes a percutaneous blood glucose sensor. The blood glucose sensor circuit 735 may include signal conditioning circuits, such as for signal filtering and signal amplification for example. If an implantable blood glucose sensor is used, the blood glucose sensor circuit 735 may include a communication circuit configured to receive blood glucose data wirelessly, such as by RF communication.

The BG management device 700 includes a second input 730 in electrical communication with the controller 115. The second input 730 receives information related to insulin delivery including an amount of active insulin, if any, and the pre-bolus correction factor. The information related to insulin delivery may be received into a memory. The correction factor module 120 determines the effective correction factor using the insulin delivery information and the sampled blood glucose data. The BG management device 700 may include a communication port 747 coupled to the second input 730. The communication port 747 receives the information related to insulin delivery from a second device. In some embodiments, the communication port 747 is a wired port such a serial interface or bus interface. In some embodiments, the communication port 747 is a wireless port such as an infrared (IR) communication port or a radio frequency (RF) communication port. The second input 730 wirelessly receives the insulin delivery data from the second device. As an example, the second device may be an insulin pump. The controller 115 is configured for communicating the effective correction factor through the communication port 747 or may display the effective correction factor on a display. In some embodiments, the BG management device may calculate the amount of insulin in the insulin correction bolus using the information related to insulin delivery and communicate the initial bolus amount, such as by a display or through the communication port for example.

In some embodiments, the user interface 105 and the second input 730 are configured to receive the information related to insulin delivery by a user manually entering the information through the user interface 105. The insulin delivery information may be obtained from a pump or may be information associated with insulin delivered by injection, such as from MDI therapy for example. The controller 115 may display the effective correction factor.

Figure 8:
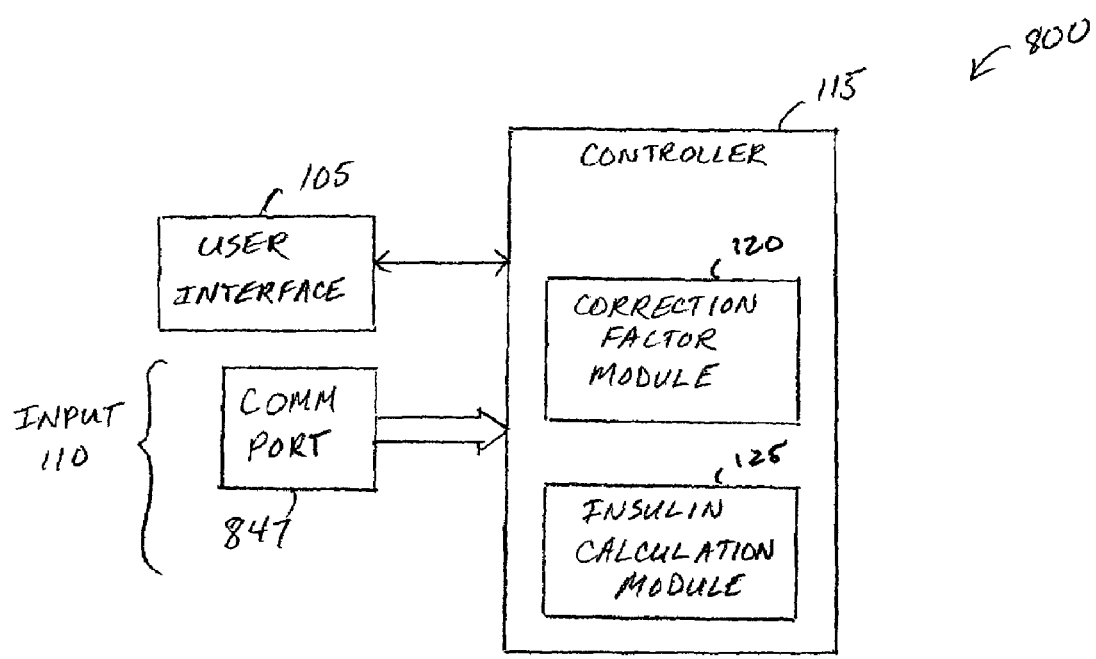
FIG. 8 is a block diagram of portions of another example of a BG management device.

FIG. 8 is a block diagram of portions of another example of a BG management device 800. BG management device 800 includes neither a GM nor an insulin pump. The BG management device 800 includes a user interface 105, an input 110, and a controller 115 in electrical communication with the input 110 and the user interface 105. The input 110 includes at least one communication port 847 configured for receiving sampled blood glucose information. The communication port 847 may provide a wired connection to a second device, or the communication port 847 may provide a wireless connection to a second device. The sampled blood glucose information may include at least one time-stamp in order to align the sampled blood glucose information to information related to insulin delivery.

The insulin delivery information may be received through the same communication port 847 or a second communication port. The communication ports may be any combination of wired or wireless communication ports. The insulin delivery information may include an amount of active insulin in the patient, if any, and the pre-bolus correction factor, and may include at least one time-stamp to align the insulin delivery information with the blood glucose information. The controller 115 may communicate the effective correction factor through the communication port and/or the controller 115 may display the effective correction factor. In some embodiments, the BG management device 800 may calculate the amount of insulin in the initial insulin correction bolus or a second bolus, if any, and communicate one or both amounts via a communication port to another device or via a display.

Method Embodiments

Figure 9:
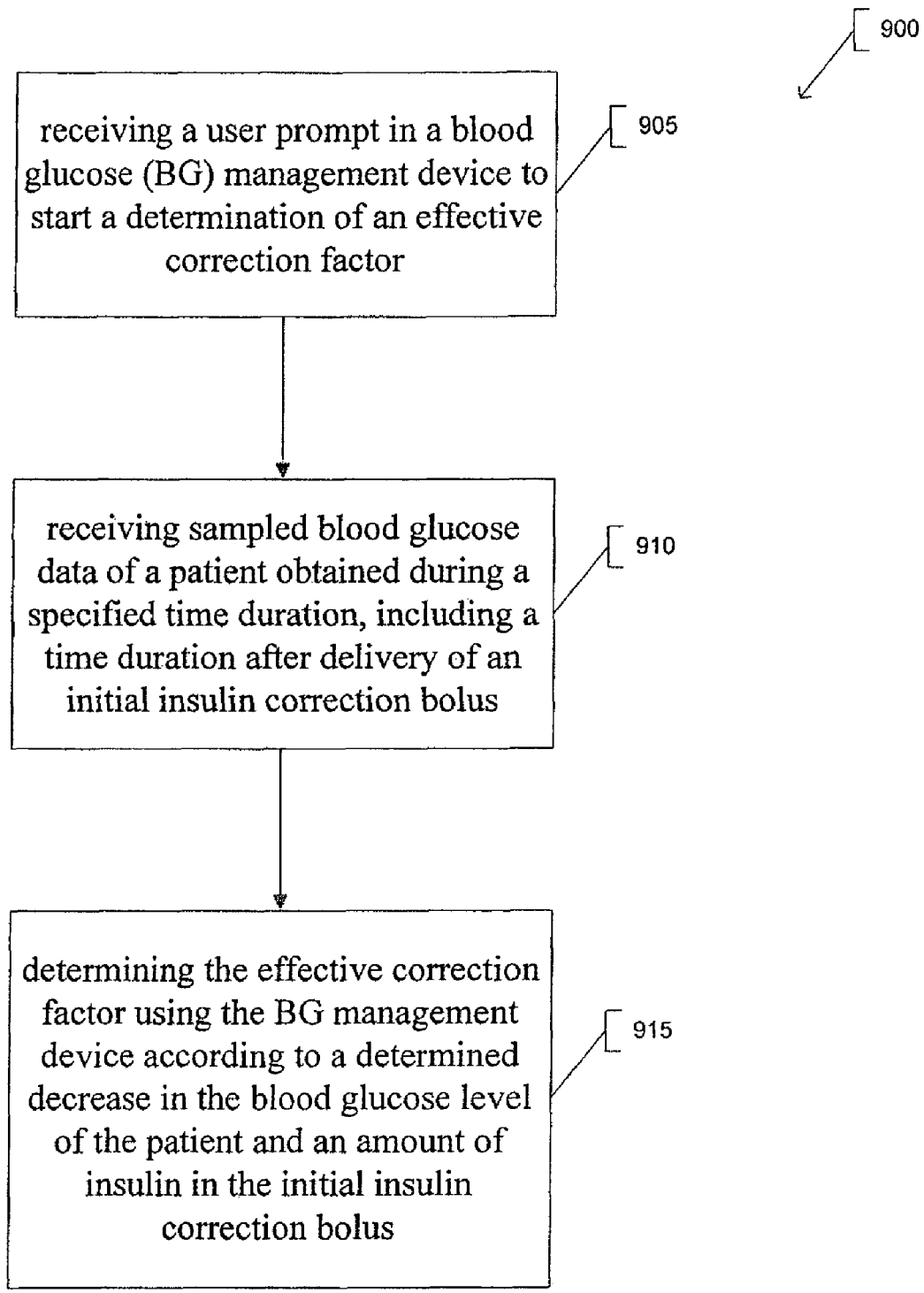
FIG. 9 is a flow diagram of a method of automatically determining a correction factor using blood glucose data.

FIG. 9 is a flow diagram of a method 900 of automatically determining a correction factor using blood glucose data. At block 905, a user prompt is received into a BG management device to start a determination of an effective correction factor. The user prompt may be received as part of a correction factor test. The user interface may include a push-button, keypad, or mouse. The user interface may also include a display to display one or more instructions for the user to execute the test, and to display an effective correction factor. At block 910, sampled blood glucose data is received in the BG management device. The blood glucose data is obtained from a patient during a specified time duration, including a time after delivery of an initial insulin correction bolus, such as a bolus delivered as part of the correction factor test. At block 915, the effective correction factor is determined using the BG management device according to a determined decrease in the blood glucose level of the patient and an amount of insulin in the initial insulin correction bolus.

In some embodiments, the method 900 includes estimating the amount of insulin in the initial insulin correction bolus. The amount of insulin is estimated using a pre-bolus correction factor and the beginning blood glucose concentration of the patient as indicated by the blood glucose data and a first specified percentage of a target blood glucose baseline. If the beginning blood glucose concentration of the patient is outside of a specified range of blood glucose levels, the method 900 may include canceling the correction factor test. In some embodiments, the amount of insulin in the initial insulin correction bolus is estimated using a rate of change of the blood glucose level of the patient as indicated by the blood glucose data. The initial insulin correction bolus is delivered to the patient using the BG management device or a second device.

In some embodiments, the method 900 includes a two-part correction factor test with the first part including the initial correction bolus and determining the effective correction factor. The initial correction bolus brings the blood glucose to a level within a first specified percentage of a target blood glucose baseline. The amount of insulin in the initial correction bolus may be estimated using a pre-bolus correction factor.

The second part of the test includes a second correction bolus to decrease a blood glucose level of the patient to within a second specified percentage of the target blood glucose baseline. The amount of insulin in the second correction bolus is estimated using the effective correction factor. The effective correction factor may be adjusted based on the amount of insulin in the second insulin correction bolus and the resulting second decrease in the blood glucose level of the patient. The amount of insulin in a correction bolus may also be determined using a rate of change of a blood glucose level of the patient.

If the blood glucose level of the patient is below the target blood glucose level, the method 900 further includes determining an amount of carbohydrates for the patient to consume. The amount of carbohydrates may be determined from how far the blood glucose level is below the target baseline. The amount of carbohydrates may also be determined using a rate of change of the blood glucose level of the patient.

According to some embodiments, the BG management device includes an insulin pump and delivers the initial insulin correction bolus and the second correction bolus if a second correction bolus is desired. The method 900 includes determining an amount of active insulin (IOB) in the patient prior to delivering the initial insulin correction bolus. In some embodiments, if an amount of active insulin is above a specified threshold active insulin amount, the BG management device may cancel the effective correction factor test. In some embodiments, if there is active insulin in the patient, the BG management device may factor in the amount of active insulin in determining the amount of insulin in the first or second correction bolus.

According to some embodiments, the BG management device includes an insulin pump and a GM. The method 900 includes automatically receiving the sampled blood glucose data from the blood glucose monitor. In some embodiments, the BG management device includes the insulin pump and the blood glucose data is obtained using a separate device. The method 900 includes receiving the sampled blood glucose data into the BG management device from the separate device through a communication port. The communication port may be a wireless port or a wired port. The separate device may be a continuous GM.

In some embodiments, the separate device may be a GM that requires some action by the user to obtain a blood glucose reading. For example, the GM may require the user to place a test strip into the GM in order to obtain a glucose reading. In some embodiments, the method 900 may include prompting the user through a user interface to obtain blood glucose data using the separate device. The prompting may be periodic during the correction factor test.

In some embodiments, the blood glucose data obtained from the separate device is entered manually into the BG management device. The method 900 includes the BG management device receiving the blood glucose data through the user interface. The user interface is configured for manual entry of blood glucose data, such as by including a keypad and a display. The user reads the blood glucose data from the separate GM and manually enters the blood glucose data into the BG management device. In some embodiments, the method 900 includes the BG management device periodically prompting the user to manually enter a blood glucose value during the determination of the effective correction factor.

According to some embodiments, the BG management device includes a GM and does not include an insulin pump. The initial insulin correction bolus (and the second correction bolus, if any), are delivered using a second separate device. The sampled blood glucose data is received automatically using the included GM. The method 900 further includes receiving information related to insulin delivery into the BG management device from the separate device.

In some embodiments, the method 900 includes receiving the insulin delivery information into the BG management device through a communication port. After a correction factor test, the BG management device may communicate the effective correction factor to the separate device using the communication port. This is useful if the separate device is an insulin pump. In some embodiments, the method 900 includes receiving the insulin delivery information into the BG management device by manually entering the insulin delivery information. The information is manually entered via a user interface on the BG management device. The effective correction factor may be displayed on the BG management device after the correction factor test.

According to some embodiments, the BG management device does not include a BG monitor or an insulin pump. The initial insulin correction bolus (and/or the second correction bolus if used) is delivered using a second separate device, such as a pump for example. The method 900 includes providing insulin delivery information, such as the amount of active insulin in the patient, if any, and the pre-bolus correction factor to the BG management device using the second device. The BG management device may calculate the initial insulin correction bolus amount using the insulin delivery information. The BG management device may display the initial insulin correction bolus amount or communicate the amount to the second device. The BG management device receives sampled blood glucose data from the second separate device or a third device. At least one of the insulin delivery information and the sampled blood glucose data includes a time-stamp to allow for alignment of the insulin delivery information and the blood glucose data. For example, the time-stamp for the insulin delivery may be the bolus delivery time. The effective correction factor is determined using the sampled blood glucose data and the insulin delivery information. The effective correction factor may be displayed or communicated to the second device.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. An apparatus comprising:
   a user interface configured to generate an electrical signal to begin determination of an effective correction factor when prompted by a user, wherein the determination of the effective correction factor includes delivery of an initial correction bolus;
   an input configured to receive sampled blood glucose data of a patient that is obtained during a specified time duration, including a time duration after delivery of the initial insulin correction bolus; and
   a controller communicatively coupled to the input and the user interface, the controller including a correction factor module configured to:
   calculate an effective correction factor using an amount of insulin in the initial insulin correction bolus and a decrease in the blood glucose level determined by the controller using the sampled blood glucose data; and
   cancel the determination of the effective correction factor if a blood glucose level of the patient is outside of a specified range of blood glucose levels.

2. The apparatus of claim 1, wherein the controller further includes an insulin calculation module configured for estimating, using a pre-bolus correction factor, the amount of insulin in the initial insulin correction bolus to decrease a blood glucose level of the patient to within a first specified percentage of a target blood glucose baseline.

3. The apparatus of claim 2, wherein the insulin calculation module is configured for receiving the pre-bolus correction factor that is manually entered by a user through the user interface.

4. The apparatus of claim 2, wherein the insulin calculation module is configured for receiving daily injection information entered by a user through the user interface and to estimate the pre-bolus correction factor using the daily injection information.

5. The apparatus of claim 2, wherein the insulin calculation module is configured for determining the amount of insulin in the initial insulin correction bolus using a blood glucose level and a rate of change of the blood glucose level of the patient.

6. The apparatus of claim 2, further including:
   a pump mechanism configured for delivering the initial insulin correction bolus to the patient, wherein the pump mechanism is operatively coupled to the controller; and
   a blood glucose monitor communicatively coupled to the input.

7. The apparatus of claim 6, wherein the blood glucose monitor is a continuous blood glucose monitor configured to automatically collect the sampled blood glucose data.

8. The apparatus of claim 6, further including:
   a display in electrical communication with the controller, and
   wherein the controller is configured for prompting the user, via the display, to begin a blood glucose measurement using the blood glucose monitor.

9. The apparatus of claim 2, further including:
   a pump mechanism operatively coupled to the controller to deliver the insulin correction bolus to the patient,
   wherein the insulin calculation module is further configured for determining an amount of active insulin in the patient, and to determine the initial insulin correction bolus amount using the amount of active insulin.

10. The apparatus of claim 1, wherein the controller includes an insulin calculation module configured to:
    estimate, using a pre-bolus correction factor, the amount of insulin in the initial insulin correction bolus to decrease a blood glucose level of the patient to within a first specified percentage of a target blood glucose baseline; and
    determine an amount of carbohydrates for the patient to consume if the blood glucose level of the patient is below a target blood glucose level.

11. The apparatus of claim 10, wherein the insulin calculation module is further configured for determining the amount of carbohydrates using a blood glucose level and a rate of change of the blood glucose level of the patient.

12. The apparatus of claim 1, further including:
a pump mechanism configured for delivering the insulin correction bolus to the patient, wherein the pump mechanism is operatively coupled to the controller; and
wherein the user interface and the input are configured to receive the sampled blood glucose data entered manually by the user.

13. The apparatus of claim 12, further including:
a display in electrical communication with the controller, wherein the controller is configured for displaying user instructions for the determination of the effective correction factor, including periodically prompting the user to enter a blood glucose value.

14. The apparatus of claim 1, further including:
a timer circuit; and
a display, wherein the timer circuit and the display are operatively coupled to the controller, and wherein the controller is configured for displaying user instructions to determine the effective correction factor at one or more specified times during a day.

15. The apparatus of claim 14, wherein the controller is configured for displaying user instructions to determine the effective correction factor during a substantially same time on multiple days.

16. The apparatus of claim 1, further including a display in electrical communication with the controller, and wherein the controller is configured for displaying the effective correction factor.

17. The apparatus of claim 1, wherein the input is a first input and the apparatus further includes:
a blood glucose sensor circuit operatively coupled to the first input, the blood glucose sensor circuit configured to produce a blood glucose signal representative of a blood glucose level of the patient and provide the sampled blood glucose data to the first input;
a second input in electrical communication with the controller, wherein the second input is configured to receive information related to insulin delivery, including an amount of active insulin, if any, and the pre-bolus correction factor; and
wherein the correction factor module determines the effective correction factor using the insulin delivery information and the sampled blood glucose data.

18. The apparatus of claim 17, further including a communication port coupled to the second input, the communication port to receive the information related to insulin delivery.

19. The apparatus of claim 18, wherein the controller is configured for communicating the effective correction factor through the communication port.

20. The apparatus of claim 17, wherein the user interface and the second input are configured to receive the information related to insulin delivery that is entered manually by the user.

21. The apparatus of claim 1, wherein the input includes at least one communication port configured for receiving the sampled blood glucose information and to receive information related to insulin delivery, including an amount of active insulin, if any, and the pre-bolus correction factor, wherein at least one of the sampled blood glucose information and the information related to insulin delivery includes a time-stamp, and
wherein the correction factor module determines the effective correction factor using the information related to insulin delivery, the sampled blood glucose data, and the time-stamp.

22. The apparatus of claim 21, wherein the controller is configured for communicating the effective correction factor through the communication port.

23. An apparatus comprising:
a user interface configured to generate an electrical signal to begin determination of an effective correction factor when prompted by a user;
an input configured to receive sampled blood glucose data of a patient that is obtained during a specified time duration, including a time duration after delivery of the initial insulin correction bolus; and
a controller communicatively coupled to the input and the user interface, the controller including:
a correction factor module configured to calculate an effective correction factor using an amount of insulin in the initial insulin correction bolus and a decrease in the blood glucose level determined by the controller using the sampled blood glucose data; and
an insulin calculation module configured to:
estimate, using a pre-bolus correction factor, the amount of insulin in the initial insulin correction bolus to decrease a blood glucose level of the patient to within a first specified percentage of a target blood glucose baseline; and
determine, using the effective correction factor, a second insulin correction bolus having an amount of insulin to decrease the blood glucose level of the patient to within a second specified percentage of the target blood glucose baseline.

24. The apparatus of claim 23, wherein the controller is configured to cancel determining the effective correction factor if a blood glucose level of the patient is outside of a specified range of blood glucose levels.

25. An apparatus comprising:
a user interface configured to generate an electrical signal to begin determination of an effective correction factor when prompted by a user;
an input configured to receive sampled blood glucose data of a patient that is obtained during a specified time duration, including a time duration after delivery of the initial insulin correction bolus; and
a controller communicatively coupled to the input and the user interface, the controller including:
a correction factor module configured to calculate an effective correction factor using an amount of insulin in the initial insulin correction bolus and a decrease in the blood glucose level determined by the controller using the sampled blood glucose data; and
an insulin calculation module configured for estimating, using a pre-bolus correction factor, the amount of insulin in the initial insulin correction bolus to decrease a blood glucose level of the patient to within a first specified percentage of a target blood glucose baseline; and
a pump mechanism configured for delivering the insulin correction bolus to the patient, wherein the pump mechanism is operatively coupled to the controller;
wherein the insulin calculation module is further configured for determining an amount of active insulin in the patient, and wherein the controller is configured to cancel the effective correction factor determination if the active insulin amount is above a specified threshold amount.

26. The apparatus of claim 25, wherein the controller is configured to cancel determining the effective correction factor if a blood glucose level of the patient is outside of a specified range of blood glucose levels.

27. An apparatus comprising:

means for receiving a user prompt in a BG management device to start a determination of an effective correction factor;

means for receiving sampled blood glucose data of a patient obtained during a specified time duration, including a time duration after delivery of an initial insulin correction bolus; and means for calculating the effective correction factor with the BG management device using a determined decrease in the blood glucose level of the patient and the amount of insulin in the initial insulin correction bolus; and means for cancelling the determination of the effective correction factor if a blood glucose level of the patient is outside of a specified range of blood glucose levels.

* * * * *